(12) United States Patent
Reichard et al.

(10) Patent No.: US 8,830,705 B2
(45) Date of Patent: Sep. 9, 2014

(54) SYSTEM AND METHOD FOR LOW SPEED CONTROL OF POLYPHASE AC MACHINE

(71) Applicant: ZBB Energy Corporation, Menomonee Falls, WI (US)

(72) Inventors: Jeffrey A. Reichard, Oconomowoc, WI (US); Nathan Jobe, Germantown, WI (US); Thomas Alan Laubenstein, Waukesha, WI (US)

(73) Assignee: ZBB Energy Corporation, Menomonee Falls, WI (US)

( * ) Notice: Subject to any disclaimer, the term of this patent is extended or adjusted under 35 U.S.C. 154(b) by 76 days.

(21) Appl. No.: 13/720,510

(22) Filed: Dec. 19, 2012

(65) Prior Publication Data

US 2013/0155730 A1  Jun. 20, 2013

Related U.S. Application Data

(60) Provisional application No. 61/577,447, filed on Dec. 19, 2011.

(51) Int. Cl.

| | |
|---|---|
| *H02M 5/458* | (2006.01) |
| *H02M 7/04* | (2006.01) |
| *H02M 7/44* | (2006.01) |
| *H02J 3/38* | (2006.01) |
| *H02P 23/03* | (2006.01) |
| *H02M 7/219* | (2006.01) |
| *H02M 5/453* | (2006.01) |

(52) U.S. Cl.
CPC ............... *H02M 5/453* (2013.01); *H02J 3/386* (2013.01); *H02P 23/03* (2013.01); *H02M 7/219* (2013.01); *Y02E 10/76* (2013.01)
USPC .................................. 363/37; 363/84; 363/95

(58) Field of Classification Search
USPC .................. 363/34, 37, 78, 80, 81, 84, 95, 97; 307/44, 64, 66; 290/44, 50, 55
See application file for complete search history.

(56) References Cited

U.S. PATENT DOCUMENTS

| | | | |
|---|---|---|---|
| 5,929,538 A | 7/1999 | O'Sullivan et al. | |
| 7,990,097 B2 * | 8/2011 | Cheng et al. | ............. 318/800 |

(Continued)

FOREIGN PATENT DOCUMENTS

| | | |
|---|---|---|
| JP | 06009400 U | 2/1994 |
| JP | 2003299396 A | 10/2003 |

OTHER PUBLICATIONS

International Search Report and the Written Opinion of the International Searching Authority, dated Apr. 24, 2013 for Application No. PCT/US2012/070655-(11 pages).

*Primary Examiner* — Adolf Berhane
(74) *Attorney, Agent, or Firm* — Boyle Fredrickson, S.C.

(57) ABSTRACT

A power converter configured to improve power capture in a wind turbine during low wind speed operation is disclosed. The power converter converts the power generated by the alternator of the wind turbine into a suitable AC current for delivery to a utility grid or to an electric load independent of the utility grid. The power converter is configured to operate in multiple operating modes, utilizing both synchronous and non-synchronous control methods, to extend the operating range of the power converter. During non-synchronous operation, the power converter utilizes a modulation routine that may either vary the dead-time compensation period during a constant modulation period or vary the modulation period with a constant on-time. A seamless transfer between non-synchronous and synchronous control methods with low total harmonic distortion (THD) improves the range of power generation for wind generators.

19 Claims, 9 Drawing Sheets

(56) References Cited

U.S. PATENT DOCUMENTS

| | | |
|---|---|---|
| 8,223,511 B2 * | 7/2012 | Cheng et al. .................... 363/35 |
| 2008/0179887 A1 | 7/2008 | Kawazoe et al. |
| 2009/0121483 A1 | 5/2009 | Xiong et al. |
| 2011/0044077 A1 * | 2/2011 | Nielsen ........................... 363/37 |
| 2011/0057444 A1 * | 3/2011 | Dai et al. ........................ 290/44 |
| 2011/0299308 A1 * | 12/2011 | Cheng et al. .................... 363/37 |
| 2011/0316490 A1 * | 12/2011 | Lang et al. ...................... 322/21 |
| 2012/0271572 A1 * | 10/2012 | Xiao et al. ....................... 702/58 |
| 2013/0033907 A1 * | 2/2013 | Zhou et al. ...................... 363/37 |
| 2013/0094258 A1 * | 4/2013 | Royak et al. .................... 363/89 |
| 2013/0107601 A1 * | 5/2013 | Wagoner et al. .............. 363/141 |
| 2013/0286692 A1 * | 10/2013 | Patel et al. ...................... 363/37 |

\* cited by examiner

SYSTEM AND METHOD FOR LOW SPEED CONTROL OF POLYPHASE AC MACHINE

CROSS-REFERENCE TO RELATED APPLICATIONS

This application claims priority to U.S. provisional application Ser. No. 61/577,447, filed Dec. 19, 2011, the entire contents of which is incorporated herein by reference.

BACKGROUND OF THE INVENTION

The subject matter disclosed herein relates to power converters and, more specifically, to improved control of and/or power conversion from polyphase alternating current (AC) machines during low speed operation.

In recent years, increased demands for energy and increased concerns about supplies of fossil fuels and their corresponding pollution have led to an increased interest in renewable energy sources. Two of the most common and best developed renewable energy sources are photovoltaic energy and wind energy. Other renewable energy sources may include fuel cells, hydroelectric energy, tidal energy, and biofuel or biomass generators. However, using renewable energy sources to generate electrical energy presents a new set of challenges.

Many renewable energy sources provide a variable supply of energy. The supply may vary, for example, according to the amount of wind, cloud cover, or time of day. Further, different energy sources provide different types of electrical energy. A wind turbine, for example, is better suited to provide Alternating Current (AC) energy while a photovoltaic cell is better suited to provide Direct Current (DC) energy. Due to the variable nature of the energy supplied as well as the varying type of energy generated, power converters are commonly inserted between the renewable energy source and the utility gird or an electrical load, if operating independently of the utility grid.

It is known that power converters have inherent losses which prevent all of the power generated by the renewable energy source from being converted to usable electrical energy. At low levels of power generation, the energy losses may be greater than the power being generated by the renewable energy source. The power converter is typically switched off to avoid an operating condition in which the power generation system is actually using more energy than it is generating.

Thus, in order to maximize the efficiency of the power generation system, it is desirable to capture energy generated at low power generation levels and to provide a converter able to efficiently operate at those low power generation levels.

BRIEF DESCRIPTION OF THE INVENTION

The subject matter disclosed herein describes a system and method for controlling polyphase machines during low speed operation and, more specifically, a system and method for controlling power transfer from an alternator while the alternator is being driven at low speeds.

According to one aspect of the present invention, improved power capture in a wind turbine during low wind speed operation is disclosed. A power converter is provided to convert the power generated by the alternator of the wind turbine into a suitable AC current for delivery to a utility grid or to an electric load independent of the utility grid. The power converter is configured to operate in multiple operating modes, utilizing both synchronous and non-synchronous control methods, to extend the operating range of the power converter. A seamless transfer between non-synchronous and synchronous control methods with low total harmonic distortion (THD) improves the range of power generation for wind generators.

The non-synchronous control method extends the low speed power transfer capability of a wind turbine. To efficiently capture power during low wind speed operation a variable frequency pulse width modulation (PWM) including dead time control approach is used. Because conventional switching methods are highly inefficient at low power levels, resulting in switching losses that exceed power production, the power converter is typically not operated during periods of low power production. The variable PWM frequency significantly reduces the losses associated with the switching of the solid state power devices during power conversion. Thus, the variable PWM frequency allows the power conversion system to capture power generated during low wind speed operation. Utilizing this PWM switching method, the usable operating range of a wind turbine is extended downward to capture this untapped power under present converter designs.

According to one embodiment of the invention, the power converter is configured to operate with wind turbines and to operate in multiple power transfer modes. During periods in which the wind is blowing above traditional cut-in speeds, a first synchronous control method transfers power from the alternator to the utility grid or electrical load. As the wind speed is reduced, the power and, consequently, the output voltage and frequency generated by the alternator are reduced. The synchronous control method reduces the modulated voltage. During periods in which the wind speed is reduced, the modulation frequency may similarly be reduced to reduce switching losses in the power converter.

As the power levels continue to drop beyond the PWM continuous switching efficiency range, additional steps may be taken to reduce power consumption in the power converter and to continue transferring power generated by the wind turbine over an increased operating range. According to one embodiment of the invention, the dead time period is increased and the maximum on time for modulation of the converter is reduced. Optionally, blanking times may be introduced at periodic intervals into the modulation method. During periods in which the modulation is disabled, the back-emf at the input of the converter may be read to obtain an electrical angle of the voltage being generated. Obtaining the back-emf during these periods extends the operating range of synchronous control of the converter. As a result, low power levels are captured and converter losses are minimized in this area of very low power utilizing the dead time compensation due to the reduction in switching losses by removing the diode recovery losses. As the power from the alternator continues to drop, control of the power switches is modified to allow for discontinuous current from the alternator. Each of the phases from the alternator are alternately connected to either the positive or the negative rail of the DC bus at a minimum on time. The current will remain somewhat sinusoidal resulting in lower torque ripple on the alternators. As a result of the multiple operating modes, the operating range of the converter is extended without excessive current spiking while not adding any detrimental effects to the wind generator.

According to one embodiment of the invention, a power converter includes an input configured to receive power from a multi-phase AC source, a DC bus having a positive and a negative rail, a plurality of positive switching devices, and a plurality of negative switching devices. Each positive switching device selectively connects one phase of the AC source to the positive rail of the DC bus, and each negative switching device selectively connecting one phase of the AC source to the negative rail of the DC bus. A memory device stores a series of instructions, and a controller is configured to execute the series of instructions. The controller executes the instructions to determine a magnitude of power generated by the AC source, and execute a modulation module to generate a positive control signal for each positive switching device and a negative control signal for each negative switching device. The control signals are generated in a first operating mode when the AC source is generating a magnitude of power greater than a first threshold, and the control signals are generated in a second operating mode when the AC source is generating a magnitude of power less than the first threshold. During the second operating mode, each of the positive switching devices are controlled to connect each phase of the AC source to the positive rail in tandem and each of the negative switching devices are controlled to connect each phase of the AC source to the negative rail in tandem. During the first operating mode the controller executes the modulation module with a fixed modulation frequency and a fixed dead time, and during the second operating mode the controller executes the modulation module with a fixed on time and a varying modulation frequency. During the second operating mode, the controller may access a lookup table stored in the memory device defining a rate of change of the modulation frequency as a function of the current modulation frequency, where the modulation frequency may vary from about 10 kHz to about 50 Hz.

According to another aspect of the invention, the control signals are generated in a intermediate operating mode when the AC source is generating a magnitude of power less than the first threshold and greater than a second threshold, and the second threshold is less than the first threshold. With the intermediate operating mode, the second operating mode executes below the first and the second thresholds. During the intermediate operating mode the controller executes the modulation module with a blanking time periodically disabling the control signals.

According to one embodiment of the invention, a power converter includes an input configured to receive power from a multi-phase AC source, a DC bus having a positive and a negative rail, a plurality of positive switching devices, and a plurality of negative switching devices. Each positive switching device selectively connects one phase of the AC source to the positive rail of the DC bus, and each negative switching device selectively connecting one phase of the AC source to the negative rail of the DC bus. A memory device stores a series of instructions, and a controller is configured to execute the series of instructions. The controller executes the instructions to determine a magnitude of power generated by the AC source, and execute a modulation module to generate a positive control signal for each positive switching device and a negative control signal for each negative switching device. The control signals are generated in a first operating mode when the AC source is generating a magnitude of power greater than a first threshold, and the control signals are generated in a second operating mode when the AC source is generating a magnitude of power less than the first threshold. During the second operating mode, the controller periodically disables the control signals for a blanking time. During the first operating mode the controller executes the modulation module with a fixed modulation frequency and a fixed dead time.

According to another aspect of the invention, the control signals are generated in a third operating mode when the AC source is generating a magnitude of power less than a second threshold, where the second threshold is less than the first threshold. During the third operating mode, each of the positive switching devices are controlled to connect each phase of the AC source to the positive rail in tandem and each of the negative switching devices are controlled to connect each phase of the AC source to the negative rail in tandem.

According to another embodiment of the invention, a method of converting power from a renewable energy source having variable power generation capability is disclosed. The method includes the steps of monitoring a level of power generated by the renewable energy source, controlling a power converter in a first operating mode via pulse width modulation having a fixed modulation frequency and a fixed dead time compensation when the level of power generated is above a first predetermined threshold, and controlling the power converter in a second operating mode via pulse width modulation module having a periodic blanking time, wherein the blanking time is repeated at a periodic interval during each cycle of a fundamental frequency of a voltage generated by the renewable energy source and wherein during the blanking time the pulse width modulation is disabled.

According to another aspect of the invention, the method includes the step of controlling the power converter in a third operating mode when the level of power generated is below a second predetermined threshold via pulse width modulation having a variable modulation frequency and a fixed on time, where the second predetermined threshold is less than the first predetermined threshold.

According to another aspect of the invention, the renewable energy source generates a multi-phase AC input voltage and controlling the power converter in the third operating mode further comprises the steps of connecting each of the phases from the AC input voltage to a positive rail of a DC bus in the power converter in tandem, and connecting each of the phases from the AC input voltage to a negative rail of a DC bus in the power converter in tandem, where each of the phases are alternately connected to the positive and negative rails.

According to yet another embodiment of the invention, a power converter includes an input configured to receive power from an AC source, a DC bus having a positive rail and a negative rail, at least one positive switching device selectively connecting the input to the positive rail of the DC bus as a function of a corresponding positive gating signal, at least one negative switching device selectively connecting the input to the negative rail of the DC bus as a function of a corresponding negative gating signal, a memory device storing a series of instructions, and a controller. The controller is configured to execute the series of instructions to execute a modulation routine to generate each of the positive and negative gating signals, determine a magnitude of power generated by the AC source, generate the positive and negative gating signals for each of the positive and negative switching devices in a first operating mode when the magnitude of power generated by the AC source exceeds a first predefined threshold, and generate the positive and negative gating signals for each of the positive and negative switching devices in a second operating mode when the magnitude of power generated by the AC source is less than the first predefined threshold. During the first operating mode, the controller periodically inserts a blanking time in the modulation routine, disabling the positive and negative gating signals during the blanking time. During the second operating mode, each of the positive switching devices connects the input to the positive rail in tandem and each of the negative switching devices connects the input to the negative rail in tandem.

According to still another aspect of the invention, during the second operating mode the controller may vary the dead time via a current controller that varies the dead-time as a function of the current transferred from the AC source to the DC bus. The controller also executes the modulation routine with a varying modulation period and a fixed on time.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which.

Figure 1:
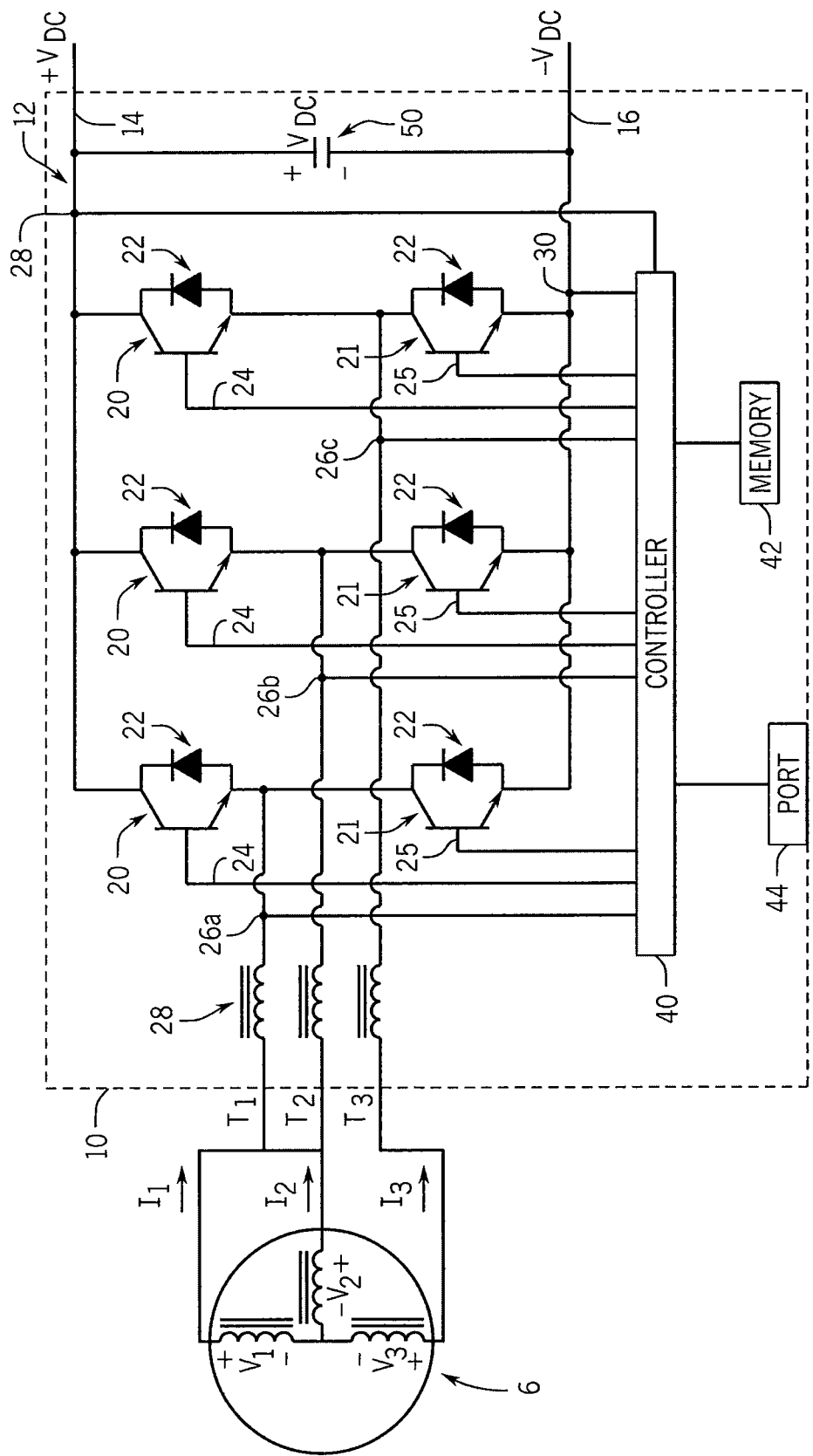
FIG. 1 is a schematic representation of a converter according to one embodiment of the invention.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Turning initially to FIG. 1, an exemplary converter 10 incorporating one embodiment of the present invention is illustrated. The converter 10 includes three input terminals, T1-T3, configured to receive input voltages. Each of the input terminals, T1-T3, of the illustrated embodiment is configured to receive one phase of a multi-phase voltage, V1-V3, generated by an alternator 6. The alternator 6 may generate, for example, three phase alternating current (AC) power. An input filter 28 is connected in series with each of the terminals, T1-T3.

The converter 10 receives the multiphase AC input voltage, V1-V3, at the terminals, T1-T3, and outputs a desired DC voltage, Vdc, present on a DC bus 12 using switching devices, 20 and 21. The DC bus 12 includes a positive rail 14 and a negative rail 16 which are made available at outputs, +Vdc and −Vdc. As is understood in the art, the positive rail 14 and the negative rail 16 may conduct any suitable DC voltage potential with respect to a common or neutral voltage and are not limited to a positive or a negative DC voltage potential. Further, either of the positive rail 14 or the negative rail 16 may be connected to a neutral voltage potential. The positive rail 14 typically conducts a DC voltage having a greater potential than the negative rail 16.

The switching devices, 20 and 21, are typically solid-state power devices. FIG. 1 shows the switching devices, 20 and 21, as bipolar junction transistors (BJTs); however, it is contemplated that any suitable switching device according to the application requirements may be used, including, but not limited to, insulated gate bipolar transistors (IGBT), field effect transistors (FET), silicon controlled rectifiers (SCR), thyristors such as integrated gate-commutated thyristors (IGCT) or gate turn-off thyristors (GTO), or other controlled devices. A diode 22 is connected in parallel to each of the switching devices, 20 and 21, for reverse conduction across the switching device, 20 and 21, as required when the switching device, 20 and 21, is turned off This diode 22 may also be a part of the semiconductor switch. For each phase of the input, a positive switch, 20, is connected between the input terminal, T1-T3, and the positive rail 14 of the DC bus 12, and a negative switch, 21, is connected between the input terminal, T1-T3, and the negative rail 16 of the DC bus 12. Each of the positive switching devices 20 are controlled by a positive gate signal 24 and each of the negative switching devices 21 are controlled by a negative gate signal 25. Each of the positive and negative gate signals, 24 or 25, is enabled or disabled to selectively permit conduction through the positive or negative switching devices, 20 or 21 respectively. A capacitance 50 is connected between the positive rail 14 and the negative rail 16 of the DC bus 12. The capacitance 50 may be a single capacitor or any number of capacitors connected in series or parallel according to the system requirements. The capacitance 50 is configured to reduce the magnitude of ripple voltage resulting from the voltage conversion between the input voltage and the DC bus 12.

A controller 40 executes a series of stored instructions to generate the gate signals, 24 and 25. The controller 40 receives feedback signals from sensors corresponding to the amplitude of the voltage and/or current at various points throughout the converter 10. The locations are dependent on the specific control routines being executed within the controller 40. For example, input sensors, 26a-26c, may provide an amplitude of the voltage present at each input terminal, $T_1$-$T_3$. Optionally, an input sensor, 26a-26c, may be operatively connected to provide an amplitude of the current conducted at each input terminal, $T_1$-$T_3$. Similarly a current and/or a voltage sensor, 28 and 30, may be operatively connected to the positive rail 14 and the negative rail 16, respectively, of the DC bus 12. The controller 40 interfaces with a memory device 42 to retrieve the stored instructions and with a communication port 44 to communicate with external devices. The controller 40 is configured to execute the stored instructions to control the converter 10 as described herein.

Figure 4:
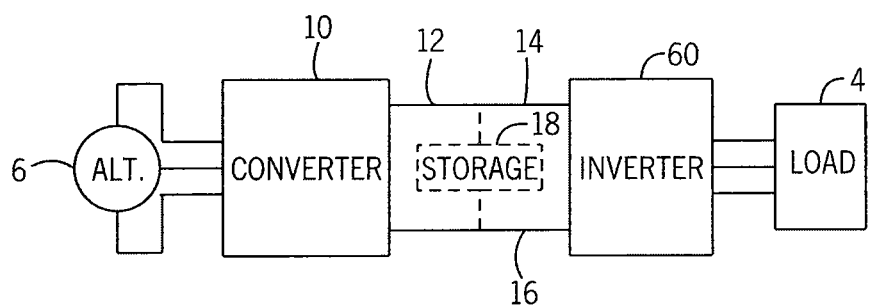
FIG. 4 is a block diagram representation of one embodiment of the invention.

Referring next to FIG. 4, an exemplary power conversion system includes a first power converter 10 and a second power converter 60, operating as an inverter, connected by a DC bus 12. Optionally, an energy storage device 18 may be connected between the positive rail 14 and the negative rail 16 of the DC bus 12. The alternator 6, such as the generator of a wind turbine, supplies power to the converter 10, which is converted to a DC voltage on the DC bus 12, and the inverter 60, in turn, supplies power to an electrical load 4 or to a utility grid (not shown) from the DC bus 12. The storage device 18 may also include a DC to DC converter to convert the DC voltage present on the DC bus 12 to a suitable DC voltage level according to requirements of the storage device. The storage device may be, for example, a lead-acid battery, a lithium ion battery, a zinc-bromide battery, a flow battery, or any other suitable energy storage device. The DC to DC converter operates to transfer energy between the DC bus 12 and the storage device 18 according to the application requirements.

Figure 2:
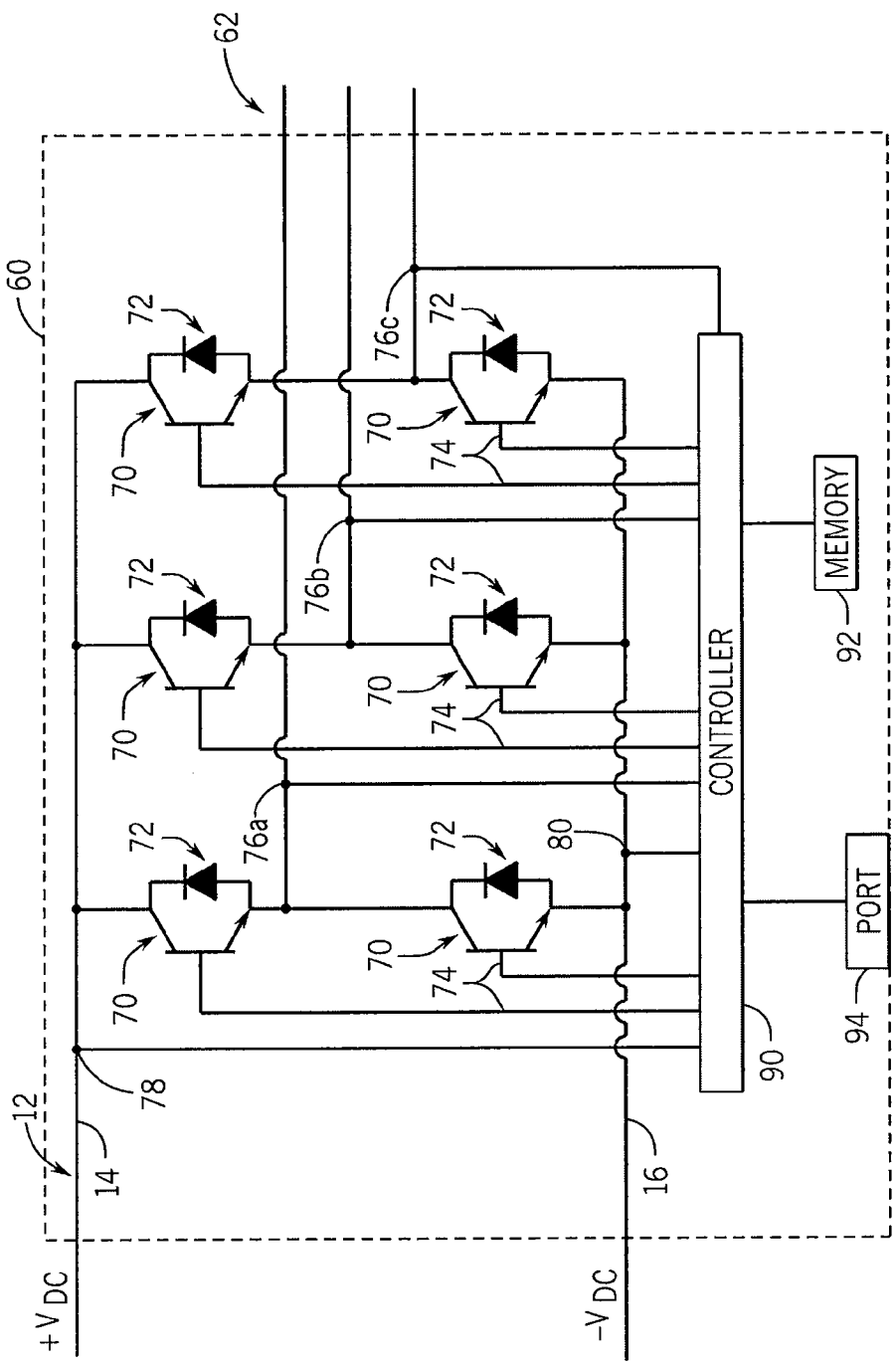
FIG. 2 is a schematic representation of an inverter according to one embodiment of the invention.

Referring now to FIG. 2, an exemplary inverter 60 is connected to the DC bus 12. The inverter 60 converts the DC voltage from the DC bus 12 to an AC voltage suitable to be supplied, for example, to the utility grid or an electrical load, such as a motor. The conversion is performed using switching devices 70 which selectively connect either the positive rail 14 or the negative rail 16 to one of the phases of the output voltage. The switching devices 70 are typically solid-state power devices. FIG. 2 illustrates the switching devices 70 as bipolar junction transistors (BJTs); however, it is contemplated that any suitable switching device according to the application requirements may be used, including, but not limited to, insulated gate bipolar transistors (IGBT), field effect transistors (FET), silicon controlled rectifiers (SCR), thyristors such as integrated gate-commutated thyristors (IGCT) or gate turn-off thyristors (GTO), or other controlled devices. A diode 72 is connected in parallel to each of the switching devices 70 for reverse conduction across the switching device as required when the switching device 70 is turned off. This diode 72 may also be a part of the semiconductor switch. Each switching device 70 is controlled by a gate signal 74. The gate signal 74 is enabled or disabled to selectively permit conduction through the switching device 70.

A controller 90 executes a series of stored instructions to generate the gate signals 74. The controller 90 receives feedback signals from sensors corresponding to the amplitude of the voltage and/or current at various points throughout the inverter 60. The locations are dependent on the specific control routines being executed within the controller 90. For example, sensors, 76a-76c, may provide an amplitude of the voltage present at each phase of the output terminal 62. Optionally, the output sensor, 76a-76c may be operatively connected to provide an amplitude of the current conducted at each phase of the output terminal 62. Similarly a current and/or a voltage sensor, 78 and 80, may be operatively connected to the positive rail 12 and the negative rail 16, respectively, of the DC bus 12. The controller 90 interfaces with a memory device 92 to retrieve the stored instructions and with a communication port 94 to communicate with external devices. According to one embodiment of the invention, the first converter 10 and the second converter 60 are separate modules having separate controllers 40, 90 and memory devices 42, 92 configured to control operation of the respective power converter. Optionally, a single controller and memory device may be configured to control operation of both power converters.

In operation, the converter 10 converts the power supplied from a variable power energy source to power available on the DC bus 12 of the converter. Subsequent energy storage devices 18 or inverter modules 60 may be connected to the DC bus 12 either to store the power generated by the energy source or to deliver stored power to an electrical load 4 (see also FIG. 4). The first power converter 10 is configured to transfer power from the source 6 to the DC bus 12 and the second power converter 60 is configured to transfer power from the DC bus 12 to the load 4. The controller 40, 90 of each power converter 10, 60 executes one or more control modules which generate gating signals 24, 25, or 74 to selectively connect the switches 20, 21, or 70, respectively, between the DC bus 12 and either the input terminals, $T_1$-$T_3$, or the output 62 according to the desired form of power conversion. According to one embodiment of the invention, a wind turbine may include blades that rotate a low speed drive shaft as a function of the speed of the wind. The low speed drive shaft is input to a gearbox, which, in turn, rotates a high speed drive shaft output as a function of its gearing. The high speed drive shaft rotates the rotor portion of the alternator 6, generating AC voltages, V1-V3, on the stator.

Figure 3:
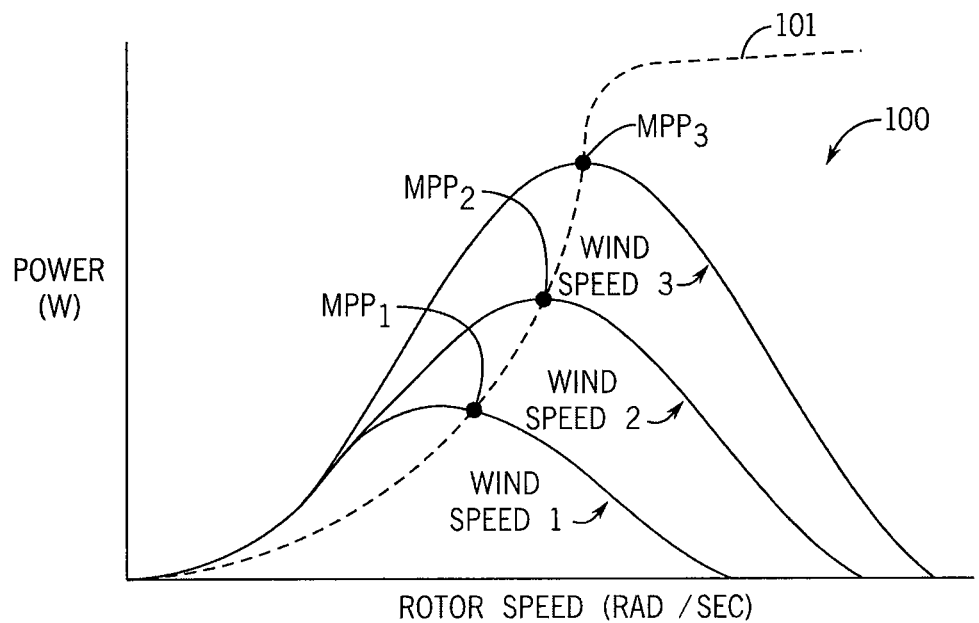
FIG. 3 is a graphical representation of the power generated by a wind turbine as functions of rotor speed and wind speed.

Referring next to FIG. 3, a graph 100 illustrates the relationship between power generated by the alternator 6 as a function of the rotor speed for an exemplary wind turbine operating under varying wind speeds. The speed of the turbine blades may be controlled, for example, by varying the pitch of the blades. Thus, for a constant wind speed, the speed of rotation of the low speed drive shaft and, consequently, the speed of rotation of the rotor in the alternator 6 can be varied. However, the potential exists that the pitch of the blades may not be adjustable at a fast enough rate to respond to varying wind conditions. In addition to, or in lieu of, pitch control, the converter 10 may help regulate the speed of the alternator 6 by regulating current drawn from the alternator 6 such that a variable braking force is applied to the alternator 6. The electronic control of the current may, therefore, compensate for variations in the wind speed to maintain operation at the maximum power point.

As further illustrated in FIG. 3 by the dashed line 101, operation of an alternator 6 may follow a squared power rule, where the power produced by the turbine increases as the square of the wind speed. For each wind speed, the controller 40 is configured to operate at a maximum power point (MPP), such that the maximum power that may be generated by the alternator at that wind speed is transferred to the DC bus 12. Tracking these maximum power points at the various wind speeds results in the exponential, squared power curve 101 until rated power production occurs. At that point, the controller 40 is configured to limit power production to the rated value to prevent damage to the alternator 6 or to the components of the converter 10. The controller 40 may be configured to execute control routines both to control the pitch of the blades and to control the current conducted between the alternator 6 and the DC bus 12. Optionally, separate controllers 40 may be used, each executing one of the control modules.

In order to regulate the current drawn from the alternator 6 during normal operating conditions, the controller 40 may implement a first current regulator configured for synchronous control of the current from the alternator 6 to the DC bus 12, as is known in the art. A synchronous current regulator receives a current reference and using measured current signals determines a current error value. The synchronous current regulator then determines a desired controlled current to compensate for the current error value. The controller 40 then determines appropriate gating signals, 24 and 25, to selectively connect each phase of the input terminals, T1-T3, to the DC bus 12 to produce the desired controlled current between the alternator 6 and the DC bus 12.

Because the alternator 6 generates AC power, the controller 40 also requires knowledge of the electrical angle of the AC voltages present at the input terminals, T1-T3. When operating above a minimum speed, the controller 40 may determine the electrical angle by detecting the back-emf present at the alternator 6. As the speed of rotation of the alternator increases, the amplitude of the back-emf similarly increases. However, the back-emf is a function of the alternator parameters as well as a function of the rotor speed. Thus, the minimum speed at which the back-emf may be detected is a function of the application. However, the amplitude of the back-emf may typically be reliably detected between about 10% and about 20% of the rated speed of the alternator 6.

Figure 5:
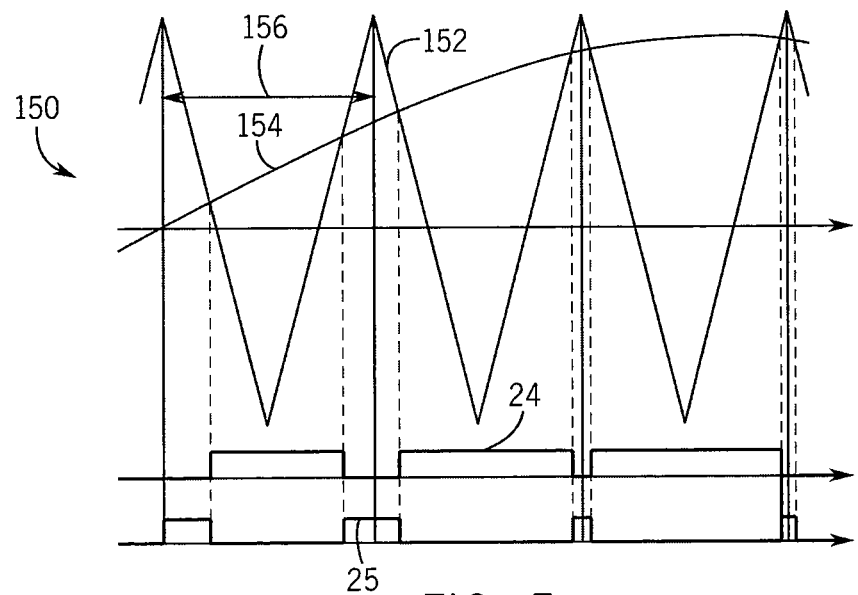
FIG. 5 is a graphical representation of a portion of one modulation period according to one embodiment of the invention.

Referring next to FIG. 5, the synchronous current regulator uses the desired controlled current value and the detected electrical angle of the alternator 6 to generate a voltage reference signal 154 to generate gating signals 24, 25. In FIG. 5, generation of gating signals 24, 25 for a segment of one cycle for one phase of the AC voltage according to an exemplary sine-triangle PWM modulation technique 150 is illustrated. In the sine-triangle PWM modulation technique 150, a triangular waveform 152 is compared to the voltage reference 154 to generate the gating signals, 24 and 25. One period of the triangular waveform 152 is defined by the switching period 156 of the PWM routine. During the switching period 156, if the voltage reference 154 is greater than the triangular waveform 152, the positive gating signal 24 is set high while the negative gating signal 25 is set low. If the voltage reference 154 is less than the triangular waveform 152, the positive gating signal 24 is set low while the negative gating signal 25 is set high. It is contemplated that other modulation techniques, as would be known to one skilled in the art, may also be used to generate the output voltage, such as space-vector or multi-level switching. Further, the modulation techniques may be implemented by comparing analog signals, as shown in FIG. 4, digital signals, such as a register being incremented up and down, or a combination thereof.

Figure 6:
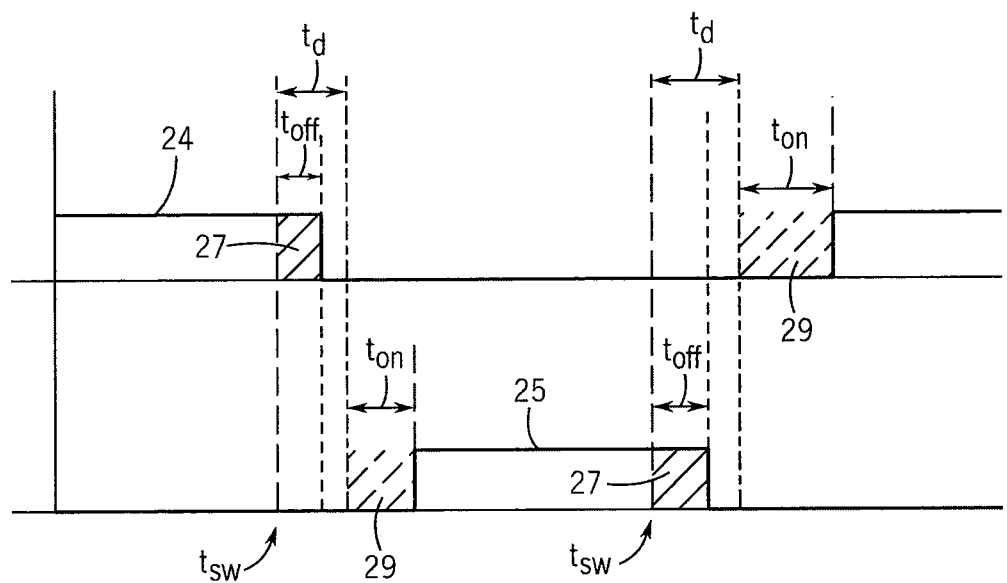
FIG. 6 is a graphical representation of dead time compensation.

FIG. 5 illustrates ideal switching conditions under which the positive gating signal 24 and the negative gating signal 25 simultaneously invert states such that the positive switch 20 and the negative switch 21 are not simultaneous conducting. In practice, however, the switches, 20 and 21, are not ideal and are not switched as indicated in FIG. 5. Referring also to FIG. 6, each of the switches, 20 and 21, requires a finite time to turn off, $t_{off}$ or to turn on, $t_{on}$. In order to prevent simultaneous conduction of the positive switch 20 and the negative switch 21, a dead time compensation may be used. The dead time, $t_d$, is typically set longer than the turn off time, $t_{off}$, of the switches, 20 or 21. When either the positive gating signal 24 or the negative gating signal 25 is commanded to turn off, as illustrated at the switching instant, $t_{sw}$, the controller 40 delays setting the other of the positive gating signal 24 or the negative gating signal 25 to on for the duration of the dead time, $t_d$, preventing simultaneous conduction of both a positive and a negative switch, 20 and 21, on the same phase, which creates a short between the positive rail 14 and the negative rail 16 of the DC bus 12. The delay in a switch, 20 or 21, turning off, $t_{off}$, results in a short period 27 of unwanted conduction and the delay in a switch, 20 or 21, turning on, $t_{on}$, results in a short period 29 of unwanted non-conduction.

As previously indicated, knowledge of the electrical angle of the AC power produced by the AC alternator 6 is required for the synchronous current regulator to control power transfer from the alternator 6 to the DC bus 12. The angular position of the alternator 6 is typically obtained from the electrical waveform generated. Using, for example, measurements of the back-emf voltage, a phase-locked loop can extract the angular position of the alternator 6. As the speed of the rotor slows, the magnitude of the back-emf decreases until the amplitude becomes too low to accurately detect. Previously, converters 10 would need to shut down to prevent instability, an inability to transfer power, and/or potential damage to the inverter resulting from generating gating signals, 24 and 25, without accurate knowledge of the electrical angle. This minimum speed at which the converter 10 could operate is also known as the cut-in speed. Although the converter 10 ceases operation, the alternator 6 is still capable of generating power below the cut-in speed.

In order to improve efficiency of the alternator 6 and to continue receiving the power generated by the alternator 6 during low-speed operation, the converter 10, as disclosed herein, executes in multiple operating modes to expand its operating range. As discussed above, the converter 10 executes a synchronous control method in a first operating mode at or above a first threshold. This first threshold corresponds to the operating speed of the alternator 6 at which the back-emf of the voltage generated by the alternator 6 may be reliably detected, which is typically about 10-20% of rated speed. During operation in the first operating mode, the modulation routine executes with a fixed period, $T_1$, and a fixed dead-time compensation, $t_d$. Optionally, the modulation frequency and, consequently, the period may vary during the first operating mode as a function of the frequency of the voltage being generated by the alternator 6. The range of switching frequency may be, for example between 5-10 kHz.

Figure 11:
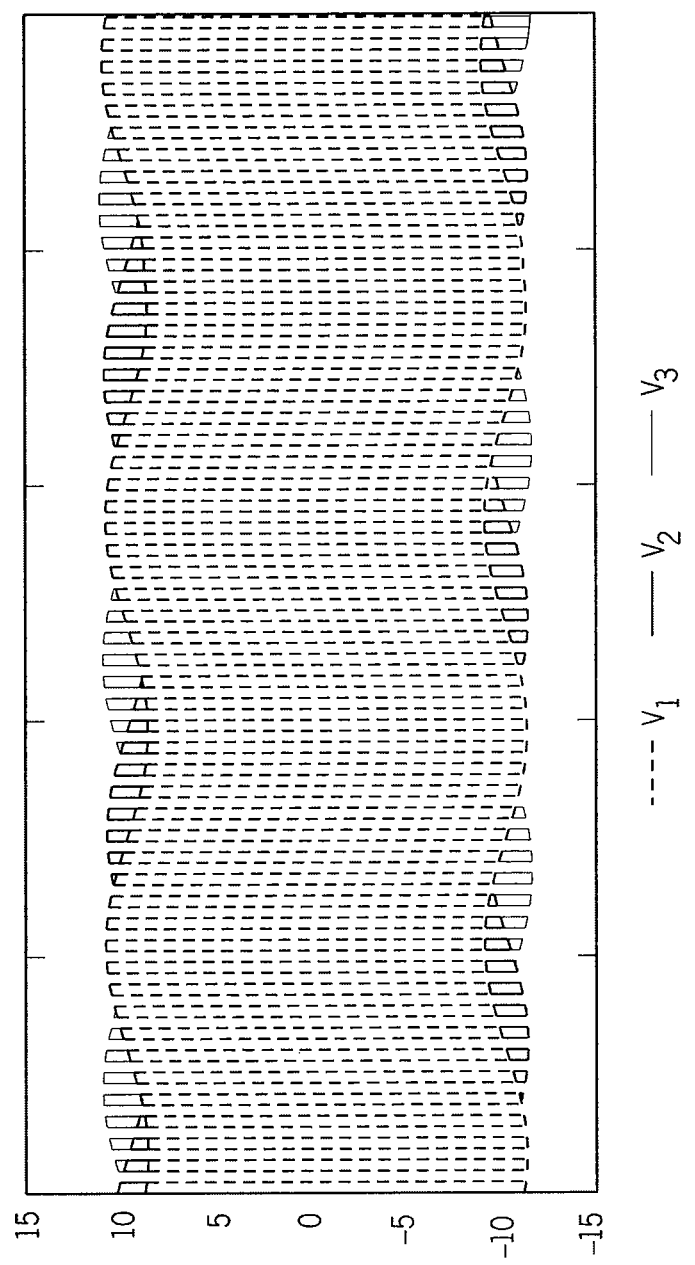
FIG. 11 is a graphical representation of a three phase voltage present at the terminals of the converter of FIG. 1 during operation under continuous pulse width modulation.
Figure 12:
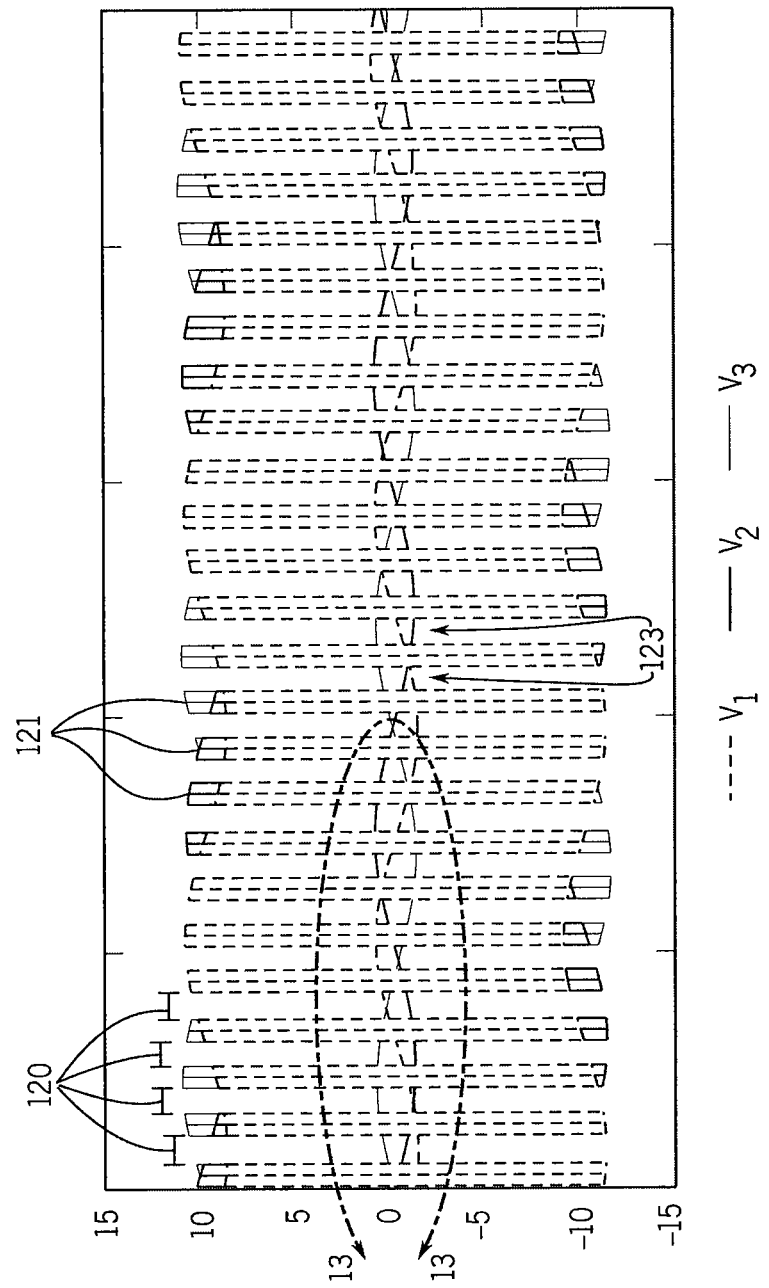
FIG. 12 is a graphical representation of a three phase voltage present at the terminals of the converter of FIG. 1 during operation under pulse width modulation with a periodic blanking time.
Figure 13:
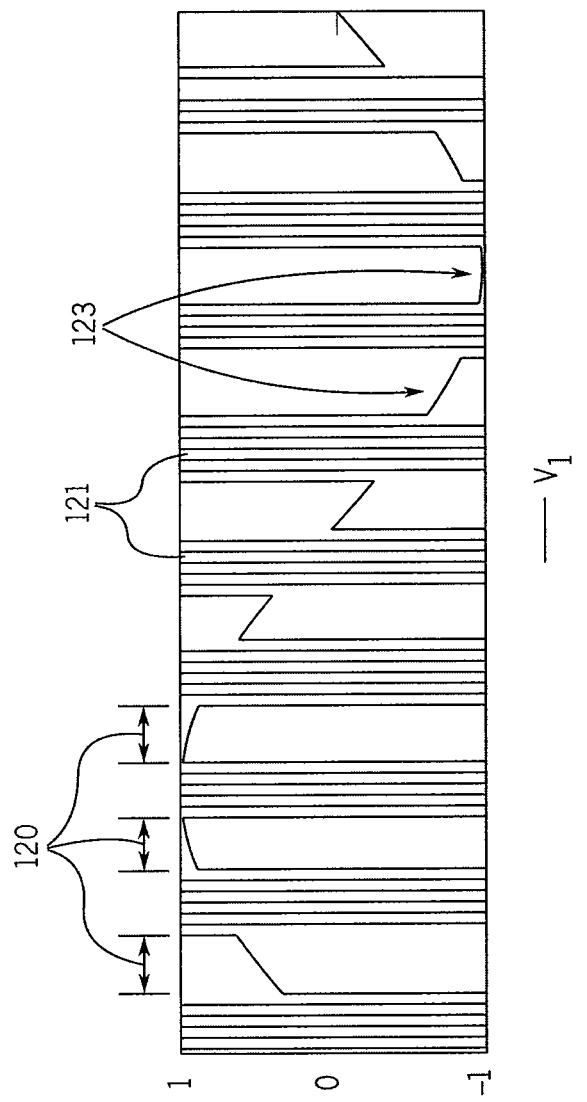
FIG. 13 is a graphical representation of one phase of the three phase voltage of FIG. 12 over one period of the voltage.

Modulation techniques control the positive switches 20 and the negative switches 21 to alternately connect each of the terminals, T1-T3, between either the positive or negative rail, 14 and 16, of the DC bus 12. Referring next to FIG. 11, the resulting modulated voltage waveforms from alternately connecting each of the terminals, T1-T3, between either the positive or negative rail, 14 and 16, of the DC bus 12 is illustrated. As the speed of the alternator 6 decreases, the frequency and amplitude of the back-emf in the alternator similarly decrease. However, because the inverter 60 connected to the power converter 10 is generating an AC voltage for connection to a utility grid or to an electrical load 4, the power conversion system maintains a generally constant level of DC voltage on the DC bus 12. Consequently, as the amplitude of the back-emf decreases, the peak amplitude of the modulated waveforms remains the same and becomes much greater than the amplitude of the back-emf generated by the alternator 6, introducing significant noise or uncertainty in attempting to read the value of the back-emf. Referring also to FIGS. 12 and 13, the difference in magnitudes of the modulated voltage 121 compared to the magnitude of the back-emf voltage 123 during low frequency operation of the alternator 6 is illustrated.

To improve the range over which the controller may reliably measure the back-emf, the controller 40 may enter a blanking control operating mode. As the operating frequency of the alternator 6 decrease, the blanking control operating mode is configured to introduce a short interval, or blanking time 120, during which the modulation is stopped. During the blanking time 120, the controller 40 may read the back-emf voltage without interference from the modulated voltage. The blanking time 120 is short enough such that the inertia of the alternator 6 and the blades of the wind turbine keep the alternator 6 rotating with little or no change in speed of the alternator 6. The blanking time 120 is introduced at a periodic interval throughout one cycle of the fundamental frequency of the voltage produced by the alternator 6. During periods of modulation, the power generated by the alternator 6 is transferred to the DC bus 12. Introduction of a blanking time, as described above, allows the power converter 10 to temporarily discontinue modulation and read the back-emf. The electrical angle of the back-emf is determined and corresponding adjustments made to the angle used by the controller 40 to perform modulation. Modulation of the switches, 20 and 21, is resumed at the modified angle to transfer power from the alternator 6 to the DC bus 12. Thus, the operating range at which the back-emf control is performed may be extended to about 5% of the amplitude of the rated speed of the alternator 6.

Figure 7:
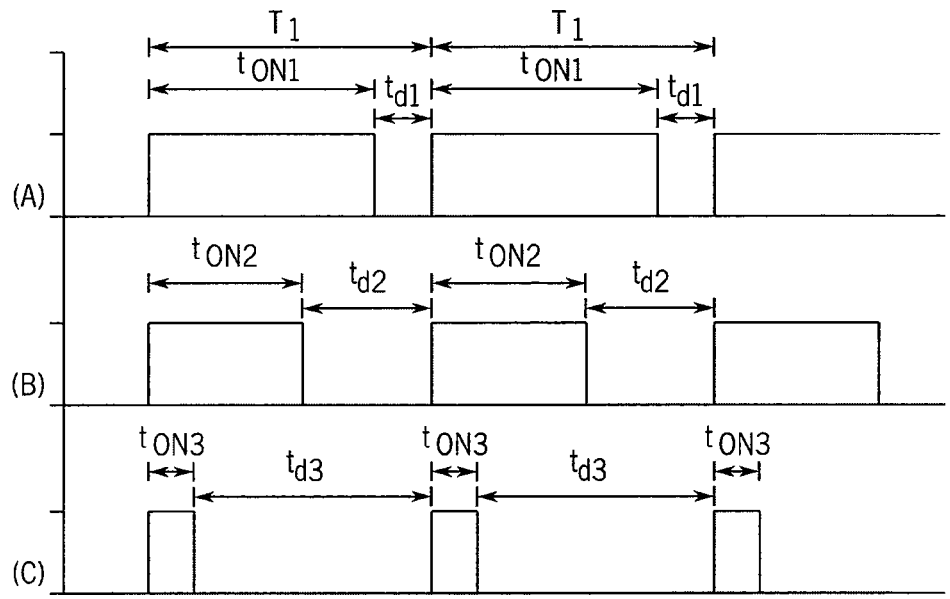
FIG. 7 is a graphical representation of dead time control with a fixed modulation period.

Referring next to FIG. 7, as the speed and, therefore, the corresponding power generated of the alternator 6 decreases, the converter may also be configured to operate in another operating mode having a fixed period, $T_1$, and varying dead-time control. The duration of the fixed period, $T_1$, is selected to be the same as the period 156 used by the controller 40 during operation in the prior operating mode. Similarly, the initial dead-time, $t_{dx}$, for dead-time control is selected to be the same as the dead time, $t_d$, used during operation in the prior operating mode. As a result, the transition from operation with the synchronous current regulator or with the current blanking control to operation with the varying dead-time has no step change in either of these operating parameters.

Although there is no step change in operating parameters, there is a change in modulation technique between operating modes. As discussed above with respect to FIG. 5, pulse width modulation generates gating signals, 24 and 25, as a function of the electrical angle of the input voltage at each terminal, $T_1$-$T_3$. As a result, the positive gate signals 24 and the negative gate signals 25 are different for each phase of the input terminals, $T_1$-$T_3$. In contrast, during dead time control, the converter 10 generates substantially identical positive gate signals 24 and negative gate signals 25 for each of the terminals, $T_1$-$T_3$. The resulting effect is that each of the positive switches 20 are turned on in tandem and each of the negative switches 21 are turned on in tandem. The controller 40 generates the gating signals, 24 and 25, such that the positive switches 20 and negative switches 21 are alternately pulsed on and off for short durations as controlled by the dead time, $t_d$.

Figure 9:
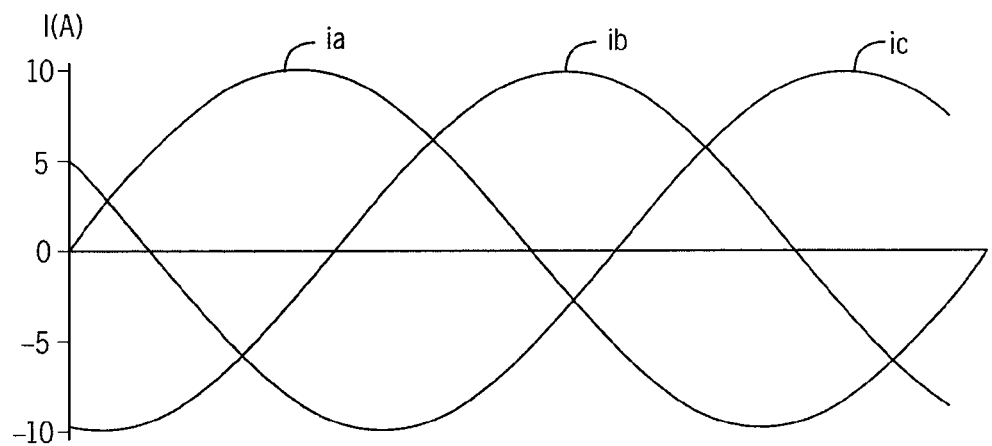
FIG. 9 is a graphical representation of a three phase alternating current of the converter of FIG. 1 operating with dead time control at a first dead time.
Figure 10:
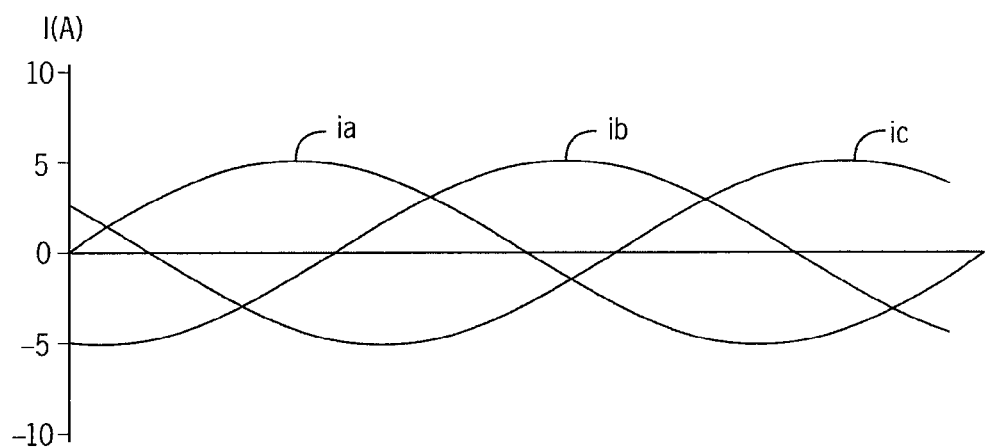
FIG. 10 is a graphical representation of a three phase alternating current of the converter of FIG. 1 operating with dead time control at a second dead time, the second dead time greater than the first dead time.

The multi-phase inductor 28 connected in series between each phase of the input terminals, $T_1$-$T_3$, and each of the switches, 20 or 21, limits the rate of change of the current. In addition, the amplitude of the voltage produced by the alternator 6 is lower at low speeds also reducing the rate of change of current through the inductor 28. Thus, although simultaneously switching each of the positive switches 20 or negative switches 21 would otherwise establish a short circuit across the alternator 6, the resulting current waveforms during this operating mode are generally sinusoidal, as illustrated in FIGS. 9 and 10.

The magnitude of the current is a function of the duration of the gating signal, 24 or 25, to each of the switches, 20 or 21 respectively. The dead-time, $t_d$, and the on time, $t_{on}$, are inversely related, meaning that as the on time, $t_{on}$, decreases, the dead-time, $t_d$, increases. The controller 40 is configured to execute a second current regulator, for example, a proportional-integral (PI) regulator used to control the dead-time, $t_d$, as a function of the current produced by the alternator 6. A progression from the longest on time, $t_{on1}$, to the minimum on time, $t_{on3}$, for operation under dead-time control is illustrated in FIG. 7, plots (a)-(c) respectively. Upon initially switching into dead time control, the alternator 6 is generating the greatest amount of energy and the greatest amount of power may be transferred between the alternator 6 and the DC bus 12. The initial on time, $t_{on}$, is, therefore, at its greatest duration. As the wind speed continues to decline, the power levels that the alternator 6 is capable of producing continues to decline, requiring a decrease in the on time, $t_{on}$, for each switch, 20 or 21. At some point, the converter reaches a minimum on time, $t_{on}$, which corresponds to a point at which the losses generated by the switches, 20 and 21, exceed the power transferred during the on time, $t_{on}$. At this point, the controller 40 begins to vary the modulation frequency.

The transition described above, allows the controller 40 to transfer into dead-time control with no step change in operating parameters. Although there is no step change in operating parameters, there is a change in modulation technique. As discussed above with respect to FIG. 5, pulse width modulation generates gating signals, 24 and 25, as a function of the electrical angle of the input voltage at each terminal, $T_1$-$T_3$. During synchronous current control, the positive gate signals 24 and the negative gate signals 25 are different for each phase of the input terminals, $T_1$-$T_3$. In contrast, during dead-time control, the converter 10 generates substantially identical positive gate signals 24 and negative gate signals 25 for each of the terminals, $T_1$-$T_3$. The resulting effect is that each of the positive switches 20 are turned on in tandem and each of the negative switches 21 are turned on in tandem. The controller 40 generates the gating signals, 24 and 25, such that the positive switches 20 and negative switches 21 are alternately pulsed on and off for short durations as controlled by the dead time, $t_d$.

The multi-phase inductor 28 connected in series between each phase of the input terminals, $T_1$-$T_3$, and each of the switches, 20 or 21, limits the rate of change of the current. In addition, the amplitude of the voltage produced by the alternator 6 is lower at low speeds also reducing the rate of change of current through the inductor 28. Thus, although simultaneously switching each of the positive switches 20 or negative switches 21 would otherwise establish a short circuit across the alternator 6, the resulting current waveforms during this operating mode are generally sinusoidal, as illustrated in FIGS. 9 and 10.

Figure 8:
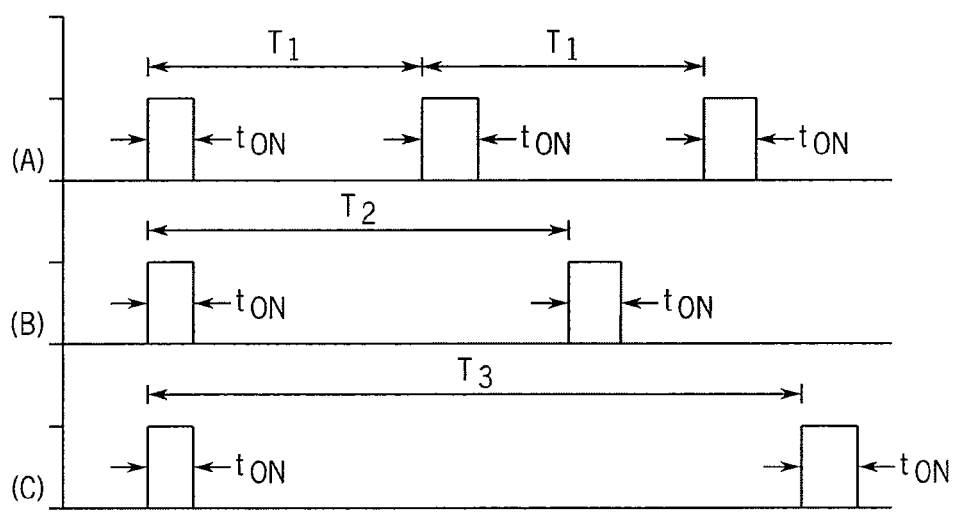
FIG. 8 is a graphical representation of a variable modulation period.

Referring next to FIG. 8, in order to continue transferring energy from the alternator 6 to the DC bus 12 after the minimum on time, $t_{on}$, has been reached, the controller 40 executes a modulation routing in which the on time, $t_{on}$, remains constant and the modulation period, T, varies. For example, plot (a) of FIG. 8 may represent the initial operating point in this operating mode. The initial period, $T_1$, is equal to the period, $T_1$, used during the transition illustrated in FIG. 7 and the on time, $t_{on}$, corresponds to the minimum on time, $t_{on3}$. As a result, the transition between operating modes again has no step changes with respect to the modulation period, T, or the on time, $t_{on}$.

As illustrated in FIG. 8, the converter 10 holds the on time, $t_{on}$, constant and controls the modulation period. The initial modulation period, $T_1$, may be, for example, 100 μsec which corresponds to a 10 kHz switching frequency. As the current provided by the alternator 6 continues to decrease, the modulation period may be extended, for example, to $T_2$ and subsequently to $T_3$. It is contemplated that the modulation period may be extended to at least 20 msec, which corresponds to a 50 Hz switching frequency. Thus, as the wind speed and the corresponding rotor speed decreases, the converter 10 continues operation across a broader operating range to increase the amount of energy obtained from the wind turbine.

During operation at variable modulation frequency, the controller 40 may access a look up table stored in memory 42 to facilitate operation because the relationship between changes in the amplitude of the current and the duration of the modulation period is nonlinear. For example, a 10 μsec change in the modulation period when operating at a 10 kHz switching frequency (i.e. a 100 μsec period) represents a greater percentage increment than when operating at a 50 Hz switching frequency (i.e. a 20 msec period). In order to improve the response time of the controller 40 to variations in the amplitude of the current during low power operation, the modulation period is changed at larger increments when the converter 10 is operating at lower switching frequencies than when the converter is operating at higher switching frequencies. The lookup table may store the desired incremental changes in the modulation frequency at varying operating points.

As the wind speed and the corresponding power produced by the alternator 6 begins to increase, the controller 40 reverses the steps through the operating modes. Initially, the controller 40 operates with a fixed on time, $t_{on}$, and reduces the modulation period, T, until it again reaches the desired duration for operation in the first and second operating modes. The transition to operation with a fixed modulation period, T, and variable on time, $t_{on}$, from operation with a variable modulation period, T, and a fixed on time, $t_{on}$, is again seamless because both operating modes encompass the common operating point. Similarly, as the wind speed and the corresponding power produced by the alternator 6 continue to increase, the dead time, $t_d$, is reduced until it reaches the dead time, $t_d$, for operation in the first operating mode. At this point, the alternator 6 is producing power at a sufficient level that the controller 40 may accurately determine the back-emf of the alternator 6. The controller begins monitoring the back-emf and determines the corresponding electrical angle, for example, using a phase-locked loop and may then switch back to operation in the first operating mode with the synchronous current regulator. Again the transition between modes is seamless because the period, T, and dead time, $t_d$, are the same for each mode at the transition point.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention

We claim:

1. A power converter comprising:
an input configured to receive power from a multi-phase AC source;
a DC bus having a positive and a negative rail;
a plurality of positive switching devices, each positive switching device selectively connecting one phase of the AC source to the positive rail of the DC bus;
a plurality of negative switching devices, each negative switching device selectively connecting one phase of the AC source to the negative rail of the DC bus;
a memory device storing a series of instructions; and
a controller configured to execute the series of instructions to:
determine a magnitude of power generated by the AC source, and
execute a modulation module to generate a positive control signal for each positive switching device and a negative control signal for each negative switching device, wherein:
the control signals are generated in a first operating mode when the AC source is generating a magnitude of power greater than a first threshold,
the control signals are generated in a second operating mode when the AC source is generating a magnitude of power less than the first threshold, and
during the second operating mode, each of the positive switching devices are controlled to connect each phase of the AC source to the positive rail in tandem and each of the negative switching devices are controlled to connect each phase of the AC source to the negative rail in tandem.

2. The power converter of claim 1 wherein during the first operating mode the controller executes the modulation module with a fixed modulation frequency and a fixed dead time.

3. The power converter of claim 2 wherein during the second operating mode the controller executes the modulation module with a fixed on time and a varying modulation frequency.

4. The power converter of claim 3 wherein the controller accesses a lookup table stored in the memory device, the lookup table defining a rate of change of the modulation frequency during the second operating mode as a function of the current modulation frequency.

5. The power converter of claim 4 wherein the modulation frequency varies from about 10 kHz to about 50 Hz.

6. The power converter of claim 3 wherein the control signals are generated in an intermediate operating mode when the AC source is generating a magnitude of power less than the first threshold and greater than a second threshold, wherein the second threshold is less than the first threshold and wherein the second operating mode executes below the second threshold.

7. The power converter of claim 6 wherein during the intermediate operating mode the controller executes the modulation module with a blanking time periodically disabling the control signals.

8. A power converter comprising:
an input configured to receive power from a multi-phase AC source;
a DC bus having a positive and a negative rail;
a plurality of positive switching devices, each positive switching device selectively connecting one phase of the AC source to the positive rail of the DC bus;
a plurality of negative switching devices, each negative switching device selectively connecting one phase of the AC source to the negative rail of the DC bus;
a memory device storing a series of instructions; and
a controller configured to execute the series of instructions to:
determine a magnitude of power generated by the AC source, and execute a modulation module to generate a positive control signal for each positive switching device and a negative control signal for each negative switching device, wherein:
the control signals are generated in a first operating mode when the AC source is generating a magnitude of power greater than a first threshold,
the control signals are generated in a second operating mode when the AC source is generating a magnitude of power less than the first threshold, and
during the second operating mode, the controller periodically disables the control signals for a blanking time.

9. The power converter of claim 8 wherein during the first operating mode the controller executes the modulation module with a fixed modulation frequency and a fixed dead time.

10. The power converter of claim 9 wherein the control signals are generated in a third operating mode when the AC source is generating a magnitude of power less than a second threshold, wherein the second threshold is less than the first threshold and wherein during the third operating mode, each of the positive switching devices are controlled to connect each phase of the AC source to the positive rail in tandem and each of the negative switching devices are controlled to connect each phase of the AC source to the negative rail in tandem.

11. The power converter of claim 10 wherein the memory device stores a lookup table defining a rate of change of the modulation frequency during the third operating mode as a function of the current modulation frequency.

12. The power converter of claim 11 wherein the modulation frequency varies from about 10 kHz to about 50 Hz.

13. A method of converting power from a renewable energy source having variable power generation capability, the method comprising the steps of:
monitoring a level of power generated by the renewable energy source;
controlling a power converter in a first operating mode via pulse width modulation having a fixed modulation frequency and a fixed dead time compensation when the level of power generated is above a first predetermined threshold; and
controlling the power converter in a second operating mode via pulse width modulation having a periodic blanking time, wherein the blanking time is repeated at a periodic interval during each cycle of a fundamental frequency of a voltage generated by the renewable energy source and wherein during the blanking time the pulse width modulation is disabled.

14. The method of converting power of claim 13 further comprising the step of controlling the power converter in a third operating mode when the level of power generated is below a second predetermined threshold via pulse width modulation having a variable modulation frequency and a fixed on time, wherein the second predetermined threshold is less than the first predetermined threshold.

15. The method of converting power of claim 14 wherein the renewable energy source generates a multi-phase AC input voltage and wherein controlling the power converter in the third operating mode further comprises the steps of:
connecting each of the phases from the AC input voltage to a positive rail of a DC bus in the power converter in tandem, and
connecting each of the phases from the AC input voltage to a negative rail of a DC bus in the power converter in tandem, wherein each of the phases are alternately connected to the positive and negative rails.

16. A power converter comprising:
an input configured to receive power from an AC source;
a DC bus having a positive rail and a negative rail;
at least one positive switching device selectively connecting the input to the positive rail of the DC bus as a function of a corresponding positive gating signal;
at least one negative switching device selectively connecting the input to the negative rail of the DC bus as a function of a corresponding negative gating signal;
a memory device storing a series of instructions; and
a controller configured to execute the series of instructions to:
execute a modulation routine to generate each of the positive and negative gating signals;
determine a magnitude of power generated by the AC source,
generate the positive and negative gating signals for each of the positive and negative switching devices in a first operating mode when the magnitude of power generated by the DC source exceeds a first predefined threshold, and
generate the positive and negative gating signals for each of the positive and negative switching devices in a second operating mode when the magnitude of power generated by the DC source is less than the first predefined threshold, wherein
during the first operating mode, the controller periodically inserts a blanking time in the modulation routine, disabling the positive and negative gating signals during the blanking time, and
during the second operating, mode each of the positive switching devices connects the input to the positive rail in tandem and each of the negative switching devices connects the input to the negative rail in tandem.

17. The power converter of claim 16 wherein during the second operating mode, the controller executes a current controller that varies the dead-time as a function of the current transferred between the AC source and the DC bus.

18. The power converter of claim 16 wherein during the second operating mode, the controller executes the modulation routine with a varying modulation period and a fixed on time.

19. The power converter of claim 18 wherein the memory device stores a lookup table defining a rate of change of the modulation period during the third operating mode as a function of the current modulation period.

* * * * *